US005185434A

United States Patent [19]

Jansen et al.

[11] Patent Number: 5,185,434

[45] Date of Patent: * Feb. 9, 1993

[54] PROLONGED-ACTION IMMUNOTOXINS CONTAINING A GLYCOPEPTIDE CONSTITUENT WHICH INACTIVATES RIBOSOMES, MODIFIED ON ITS POLYSACCHARIDE UNITS

[75] Inventors: Franz Jansen, Castries; Pierre Gros, Montpellier, both of France

[73] Assignee: Sanofi, Paris, France

[ * ] Notice: The portion of the term of this patent subsequent to Mar. 27, 2007 has been disclaimed.

[21] Appl. No.: 317,864

[22] Filed: Mar. 2, 1989

Related U.S. Application Data

[63] Continuation of Ser. No. 804,438, Dec. 4, 1985, abandoned.

[30] Foreign Application Priority Data

Feb. 13, 1985 [FR] France ................................ 85 02068

[51] Int. Cl.[5] .......................... C07K 15/28; C07K 3/06

[52] U.S. Cl. ................................ 530/391.7; 530/391.5; 530/391.1; 530/391.9; 530/402; 530/403; 530/404; 530/405; 530/406; 530/395; 530/396; 424/85.91

[58] Field of Search ................................ 530/389-391, 530/402-406, 395, 396, 391.1, 391.5, 391.7, 391.9; 514/2, 8, 21, 885; 424/85.91

[56] References Cited

U.S. PATENT DOCUMENTS 4,340,535 7/1982 Voisin et al. ...................... 424/85.91
4,749,566 6/1988 Casellas et al. .................. 424/85.91

OTHER PUBLICATIONS

Vitetta et al, *Cancer Drug Delivery*, 2(3) 1985, pp. 191-198 Collier, 190th ACS National Meeting Sep. 8-13, 1985 (abst only).

*Primary Examiner*—Garnette D. Draper
*Attorney, Agent, or Firm*—Bacon & Thomas

[57] ABSTRACT

Prolonged-action immunotoxin consisting of a conjugate in which an antibody or antibody fragment is coupled, by means of a covalent structure containing a disulfide group or a thioether group, with a glycoprotein which inactivates ribosomes and has a prolonged action obtained by the oxidation of its saccharide units which periodate ions.

19 Claims, 3 Drawing Sheets

Plasma elimination of A chain, of oxidized A chain

Influence of the treatment time with sodium periodate on the plasma concentration of A chain Plasma elimination of gelonine and oxidized gelonine Plasma elimination kinetics of IT101 and IT(A-1a)T101

Cytotoxicity of IT(A-1a)T101 and (A-1a) on CEM cells, measured by the inhibition of protein synthesis Cytotoxicity of IT(A-1a)T101 and IT T101 on CEM cells, measured by the clonogenic test

PROLONGED-ACTION IMMUNOTOXINS CONTAINING A GLYCOPEPTIDE CONSTITUENT WHICH INACTIVATES RIBOSOMES, MODIFIED ON ITS POLYSACCHARIDE UNITS

This application is a continuation of application Ser. No. 804,438 filed Dec. 4, 1985 now abandoned.

The present invention relates to new medicinal molecules containing at least one antibody covalently bonded to a constituent of polypeptide type which inhibits protein synthesis and is derived from a glycoprotein (or a glycopeptide) whose polysaccharide units have been modified.

U.S. Pat. No. 4,340,535 and French Patent Application No. 81/07596 and No. 81/21836 describe the preparation of anticancer products, called conjugates, which are obtained by the coupling, by means of a covalent bond, of the A chain of ricin with antibodies or antibody fragments directed against antigens carried by the cell to be destroyed. The products of this type have been designated, and are designated in the present Application, by the generic name of immunotoxins.

Conjugates analogous to the previously described immunotoxins containing the A chain of ricin are known which are also suitable as anticancer drugs and result from the coupling, by means of a covalent bond, of antibodies or antibody fragments with other glycoproteins which inactivate ribosomes, such as, in particular, the gelonine extracted from Gelonium multiflorum (Eur. J. Biochem. 1982, 116, 447–454; Cancer Res. 1984, 44, 129–133) or the inhibitor extracted from Momordica charantia (MOM) (U.S. Pat. No. 4,368,149).

These glycoproteins which inactivate ribosomes (abbreviated to GPIR), and which have properties similar to those of the A chain of ricin, are substances with a molecular weight of the order of magnitude of 20,000 and 30,000 (Cancer Survey, 1982, 1, 489–520).

The term "glycoprotein which inactivates ribosomes", as used in the present description and also in the claims, denotes any substance which carries saccharide units belonging to the class of macromolecules which inactivate ribosomes and consequently inhibit protein synthesis in eucaryotic cells, as well as any fragment of the said substance which possesses the same inactivating property, it being possible for the said glycoprotein which inactivates ribosomes to be of natural or biosynthetic origin, being derived from a cell whose genotype has been modified for this purpose.

It is also known that the cytotoxic activity of these immunotoxins can be potentiated by a variety of adjuvant substances such as ammonium salts, various amines or certain carboxylic ionophores such as monensin or nigericin.

However, the therapeutic effects of immunotoxins, whether activated or not, can only manifest themselves fully on condition that the immunotoxin is capable, through its antibody part, of becoming localized in vivo, in the active form, on the target cells to be destroyed (sine qua non condition for any expression of immunotoxin activity). The capability of the immunotoxin to become localized on the target depends first and foremost on the ability of the immunotoxin to remain in the bloodstream and the extracellular fluids, in the active form, for sufficient lengths of time for it to reach its target cells and at sufficient concentrations to give a high degree of occupation of the corresponding antigen sites.

Numerous studies have made it possible to establish the plasma elimination kinetics of immunotoxins after intravenous injection into various animal.models. It has been found that, after injection, the plasma level of biologically active immunotoxin decreases very rapidly and very substantially. Thus, in a typical case involving rabbits, in a model using an immunotoxin built up by coupling the A chain of ricin, by means of a link containing a disulfide bridge, with a monoclonal antibody directed against the antigen T65 of human T lymphocytes (antibody T101), it is found that 97% of the immunotoxin present in the bloodstream at time 0 after injection disappears in 30 minutes and 99.9% disappears in 17 hours. This rapid disappearance of the immunotoxin quite obviously detracts from the expression of its complete cytotoxic capacity, the immunotoxin being prevented from durably saturating a high proportion of the target antigens carried by the cells to be destroyed. Moreover, a comparison of the plasma elimination kinetics of immunotoxins with those of the corresponding unconjugated antibodies shows by contrast that—as is well known—the antibodies remain in the plasma at a high level for relatively long periods of time. Now, even in the most highly purified immunotoxin preparations, there is always a certain residual level of unconjugated antibodies. Due to the effect of the differential rates of elimination of immunotoxins and antibodies, the unconjugated antibodies, which are initially very much in the minority, progressively become the majority component after a few hours, so these antibodies gradually compete to become powerful antagonists for the fixation of the immunotoxins to their targets.

Therefore, this clearly shows the value of enhancing the persistence of immunotoxins in the plasma, in their active form, so as to increase both the duration and degree of occupation of the target antigens and consequently to improve the therapeutic effects of the immunotoxins.

Furthermore, experiments involving in vivo localization of the immunotoxin containing the A chain of ricin, radiolabeled and then injected into animals with no specific target, have shown that the conjugate becomes localized preferentially in the liver during the first few minutes after injection. The same applies to the A chain of ricin, which follows the same pattern when injected in the uncoupled form. This strongly suggests that the immunotoxin becomes fixed in the liver via the cytotoxic sub-unit contained in the immunotoxin.

It is known that the A chain of ricin is a glycoprotein whose polyosidic groups comprise especially mannose residues and N-acetylglucosamine residues, some mannose residues being in terminal positions (Agri. Biol. Chem., 1978, 42, 501). Also, receptors capable of recognizing glycoproteins containing these terminal mannose residues have been found to exist in the liver. It has also been shown that the glycoproteins recognized by these receptors—the latter being present essentially on the Kupffer cells—are rapidly eliminated from the bloodstream by fixation to these cells, which metabolize them. This is well documented especially in the case of beta-glucuronidase and in the case of ribonuclease B (Arch. Biochem. Biophys., 1978, 188, 418; Advances in Enzymology, published by A. Meister, New York, 1974; Pediat. Res., 1977, 11, 816).

Taken as a whole, this information shows that the rapid elimination of immunotoxins containing the A chain of ricin can be explained by the recognition of the mannose residues of the A chain of ricin by the hepatic cells and in particular the Kupffer cells. The studies of plasma elimination kinetics carried out on other GPIRs, for example gelonine or MOM, after intravenous injection into the animal, have shown that, as in the case of the A chain of ricin, the plasma level of GPIR decreases very rapidly and very substantially after injection. Thus, in a typical case involving rabbits, after the injection of gelonine purified by the method described (J. Biol. Chem., 1980, 255, 6947–6953), it is found that 93% of the gelonine present in the bloodstream at time 0 after injection disappears in 1 hour and 99.99% disappears in 24 hours.

It is known that the oxidation of osidic structures, including those contained in glycoproteins, with periodate ions causes the scission of the carbon chain wherever two adjacent carbon atoms carry primary or secondary hydroxyls. If the two adjacent hydroxyls are secondary, as is generally the case in the cyclic oses present in GPIRs, oxidation produces two aldehyde groups on the carbons between which the scission has taken place.

In the description, the term "periodate" denotes the $IO_4^-$ ion, which is also found in the literature under the name of "metaperiodate".

It has now been found, absolutely unexpectedly, that if the carbohydrate units of a glycoprotein which inactivates ribosomes are modified by oxidation with periodate ions, a new glycoprotein which inactivates ribosomes is obtained which has the dual property of retaining its biological activities and of being eliminated very slowly from the bloodstream in vivo.

It has also been found that if these new prolonged-action glycoproteins which inactivate ribosomes are coupled with antibodies, the resulting conjugates retain the known biological properties of immunotoxins and exhibit slow plasma elimination kinetics.

The present invention therefore relates to products, belonging to the class of immunotoxins, which are obtained by the covalent coupling of, on the one hand, an antibody or antibody fragment, used in its natural form or correctly modified, with, on the other hand, a prolonged-action glycoprotein which inactivates ribosomes.

For the sake of clarity, the meaning of the symbols used to denote the different proteins or their radicals, and of expressions used to denote the different symbols, is specified below.

The symbol P represents a protein chosen from the group comprising any antibody or antibody fragment, any immunogloblulin or immunoglobulin fragment or any molecule derived from the above by artificial modification of any one of their functional groups, including carbohydrate structures which they carry, with the proviso that the protein chosen in this way remains capable of selectively recognizing a given antigen on the surface of the cells carrying this antigen, especially the target cells. The starting protein P can be of natural or biosynthetic origin, being derived from a cell whose genotype has been modified for this purpose.

The symbol GPIR-la represents a protein which is a prolonged-action glycoprotein which inactivates ribosomes, obtained by treatment of a glycoprotein which inactivates ribosomes, the thiol groups of which are optionally protected, with an aqueous solution of an alkali metal periodate, for a period of 0.2 to 24 hours, at a temperature of 0° to 15° C. and in the absence of light, and by unblocking of the thiol groups, if appropriate, or any molecule derived from the said glycoprotein by artificial modification of any functional group carried by this protein, with the proviso that the protein chosen in this way still has the property of inhibiting ribosomal protein synthesis in eucaryotic cells, as can be demonstrated in an acellular study model. In the immunotoxin, the part GPIR-la is also denoted as a "cytotoxic subunit".

The symbol A-la represents a prolonged-action glycoprotein which inactivates ribosomes, obtained by treatment of the A chain of ricin, in which at least one of the thiol groups of its cysteines 171 and 257 is optionally protected, with an aqueous solution of an alkali metal periodate, for a period of 0.2 to 24 hours, at a temperature of 0° to 15° C. and in the absence of light, and by deprotection of the said thiol group, if appropriate.

The symbol P' represents a radical derived from the above protein P, as such or appropriately chemically modified, from which one or more of its own groups have been removed and in which other functional groups are optionally blocked.

The symbol GPIR-1a' represents a radical derived from the above protein GPIR-1a, as such or appropriately chemically modified, from which one or more of its own groups have been removed and in which other functional groups are optionally blocked.

The symbol A-1a' represents a radical derived from the protein A-1a, from which at least one of the thiol groups of its cysteines 171 and 257 have been removed.

The symbol $P_1$ represents one of the proteins GPIR-1a and P as defined above, which carries free thiol groups attached to the said protein directly or via a spacing structure.

The symbol $P_2$, which is different from $P_1$, represents one of the proteins GPIR-1a and P as defined above, which carries one or more functional groups capable of reacting with the free thiols.

The symbol $P_1$, represents that radical of the protein $P_1$ which is bonded to the groups belonging to the protein $P_1$, especially the groups SH (of the cysteine), $NH_2$ (in the terminal position of the protein or in the epsilon position of the lysines), OH (of the tyrosines) or COOH (of the aspartic and glutamic acids), or, only in the case where $P_1$ is an antibody or antibody fragment, that radical of the protein $P_1$ which originates from the opening of the carbohydrate structures by reaction with periodic acid according to known methods.

The symbol $P_2$, represents that radical of the protein $P_2$ which is bonded to the characteristic functional groups $NH_2$ (in the terminal position of the protein or in the epsilon position of the lysines), OH (of the tyrosines) or COOH (of the aspartic and glutamic acids).

For example, $P_{1'}$—SH represents the protein $P_1$ (which can arbitrarily be the antibody or antibody fragment P or the protein GPIR-1a) in which the SH groups of the cysteines are free and the other functional groups are optionally blocked.

In the same way, $P_{1'}$—CO— represents the protein $P_1$ in which the terminal carboxyl group or the carboxyl groups of its glutamic and aspartic acids are coupled with a group which artificially introduces an SH group.

Again, $P_{2'}$—NH— represents the protein $P_2$ (which can arbitrarily be the antibody or antibody fragment P or the protein GPIR-1a) in which the terminal amino group or the amino groups of its lysines are attached to a group capable of coupling with the thiol of the protein $P_1$.

The term "inert spacing structure", as used here for E and E′, denotes a divalent organic radical which is inert towards the reactants used in the process, such as a straight-chain or branched alkylene group containing from 1 to 15 carbon atoms, which can contain one or more double bonds, can be interrupted by oxygen atoms or can be substituted by one or more inert functional groups such as methoxy groups, free or esterified carboxyl groups, dialkylamino groups or carbamate groups. The same term also denotes an arylene group containing from 6 to 15 carbon atoms, which can be substituted by one or more inert functional groups as indicated above for the alkylene group.

The expression "functional group capable of bonding covalently", as used here for Y and Y′, denotes any groups capable of reacting with the groups belonging to the proteins $P_1$ and $P_2$ to give a covalent bond. Thus, the groups —CO— and —(C=NH)— are suitable functional groups capable of bonding with the free amines, the thiols and the phenolic hydroxyls of the proteins. Likewise, the —NH— group is a suitable functional group capable of bonding with the free carboxyl groups of the proteins. The group =NH— is a suitable functional group capable of bonding with the two carbon atoms of the carbohydrate structures of the proteins $P_1$ and $P_2$ after oxidation with periodate ions, but only in the case where $P_1$ and $P_2$ are an antibody or an antibody fragment.

The expression "group belonging to the proteins", as used here for Z and Z′, denotes the radicals originating from the characteristic groups of the amino acids forming the proteins $P_1$ and $P_2$, such as the oxygen atom originating from the hydroxyls of the tyrosine and possibly serine amino acids, the carbonyl group originating from the terminal carboxyl or the free carboxyls of the aspartic and glutamic acids, the —NH— group originating from the terminal amine of the proteins, for example the lysine, or the sulfur atom originating from the thiol of the cysteine. The same expression also denotes the group originating from the dialdehyde structure obtained after oxidation of one of the carbohydrate structure of the proteins $P_1$ and $P_2$ by treatment with periodate ions, but only in the case where $P_1$ and $P_2$ are an antibody or antibody fragment.

The term "activating radical", as used here for X, denotes a group boned to an —S—S— bridge and capable of reacting with a free thiol to form a disulfide with the release of X-SH. Suitable activating radicals are pyridin-2-yl and pyridin-4-yl group which are unsubstituted or substituted by one or more halogens or alkyl, carboxyl or alkoxycarbonyl radicals; the phenyl group which is unsubstituted or, preferably, substituted by one or more halogens or nitro, alkoxy, carboxyl or alkoxycarbonyl groups; or an alkoxycarbonyl group such as methoxycarbonyl.

The terms "alkyl" and "alkoxy" denote groups containing up to 5 carbon atoms.

The term "alkylene" denotes straight-chain or branched saturated aliphatic groups containing up to 10 carbon atoms, which can be substituted by one or more inert functional groups such as alkoxycarbonyl groups.

More particularly, the present invention relates to products, belonging to the class of the immunotoxins, which are obtained by the covalent coupling of, on the one hand, an antibody or antibody fragment, used in its natural form or correctly modified (symbol P), which possesses the capacity to selectively recognize an antigen carried by the intended target cells, with, on the other hand, a prolonged-action glycoprotein which inactivates ribosomes, obtained by treatment of a glycoprotein which inactivates ribosomes, the thiol groups of which are optionally protected, with an aqueous solution of an alkali metal periodate, for a period of 0.2 to 24 hours, at a temperature of 0° to 15° C. and in the absence of light, and by unblocking of the thiol groups, if appropriate (symbol GPIR-1a), the coupling of the 2 proteins being effected either via a disulfide bond or via a thioether bond.

An immunotoxin formed by the coupling of an antibody P with a prolonged-action glycoprotein which inactivates ribosomes, GPIR-1a, can be represented by the following statistical formula:

P′-W-GPIR-1a′ I in which P′ represents the radical of a protein which is an antibody or an antibody fragment P, as such or appropriately chemically modified, in which other functional groups are optionally blocked, GPIR-1a′ represents the radical of a protein which is GPIR-1a, as such or appropriately chemically modified, in which other functional groups are optionally blocked, and W represents a divalent covalent structure containing a thioether group or a disulfide group in which either the sulfur atoms are those of the cysteines of P and GPIR-1a or they are bonded to the groups belonging to P and/or GPIR-1a by spacing structures carrying a functional group bonded to the said groups belonging to P and/or GPIR-1a.

A thioether bond between two proteins is understood as meaning a bond of the type:

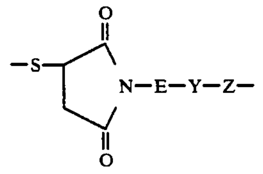

in which Z, Y and E are as defined below.

The present invention preferentially relates to an immunotoxin of the statistical formula:

P′-W′-GPIR-1a′ II in which P′ and GPIR-1a′ are as defined above and W′ represents a covalent structure chosen form:

(a) a group of the formula:

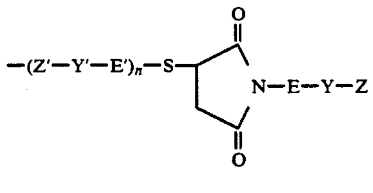

(b) a group of the formula:

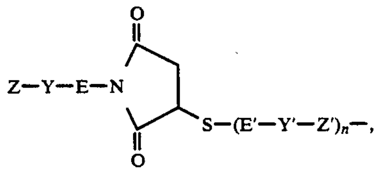

(c) a group of the formula:

$—Z—Y—E—S—S—(E'—Y'—Z')_n—$ or (d) a group of the formula:

$—(Z'—Y'—E')_n—S—S—E—Y—Z—,$ in which:

Z and Z' represent the groups belonging to the proteins GPIR-1a and P, chosen from the oxygen atom originating from the hydroxyl of one of the tyrosine residues, the carbonyl group originating from one of the terminal carboxyls or the free carboxyls of the aspartic and/or glutamic acids of GPIR-1a and P, the —NH— group originating from one of the terminal amines of GPIR-1a and P or from one of the amines in the epsilon position of one of the lysine residues, and, only for Z in the covalent structure (b) and (c), the group originating from the dialdehyde structure obtained after oxidation of one of the carbohydrate structures of P with periodic acid according to the known methods;

Y and Y' represent functional groups capable of bonding covalently with any one of the groups Z and Z' of the proteins GPIR-1a and P;

E and E' represents inert spacing structures; and n represents zero or 1.

The immunotoxins are represented in simplified form by the formulae I and II above, but it is understood that the divalent covalent structure —W— or —W'— is bonded to at least one molecule P and at least one molecule GPIR-1a. The number of bonds with the proteins P and GPIR-1a depends on the number of groups belonging to the said proteins which are involved in the coupling operation.

For example, if an immunotoxin is formed by the coupling of the sub-unit A of native ricin with the antibody P (for example the antibody T101) via a divalent covalent structure having a disulfide group in which one sulfur is that belonging to the cysteine 257 of the prolonged-action A chain of ricin and the other is bonded to the phenolic oxygens of the tyrosines of the antibody P by an oxopropyl group, it will have the statistical formula:

$P'(O—CO—CH_2—CH_2—S—S—A—1a')_t$ in which t represents the number of tyrosines in the antibody (for example the antibody T101) which are involved in the coupling.

The resulting immunotoxin thus corresponds to a product of the formula II in which:

P' is as defined above, especially the radical of the antibody T101 from which the phenolic groups of the tyrosines involved in the coupling have been removed;

A-1a' is the radical of the prolonged-action A chain of ricin from which the thiol group of its cysteine 257 has been removed; and W' is the group (c):

$—Z—Y—E—S—S—(E'—Y'—Z')_n—$ in which Z is the oxygen of the phenolic hydroxyls involved in the coupling, Y is —CO—, E is the inert spacing structure $—CH_2—CH_2—$ and n is zero.

Particular preference is given to the immunotoxins formed by one or more structures containing the prolonged-action sub-unit A of ricin and a single antibody P, which are represented by the statistical formula:

$$p'(W'\text{-}A\text{-}1a')_m \qquad \text{III}$$

in which P', W' and A-1a' are as defined above and m represents the number of groups belonging to the protein P which are involved in the coupling. The number m varies from 0.3 to 12, preferably from 0.5 to 10.

The expression "m varies from 0.3 to 12, preferably from 0.5 to 10" means that the value of m is a statistical value because the coupling does not take place homogeneously within the population of antibody molecules. The number m may therefore not be an integer.

The value of m depends especially on the antibodies used and more particularly on their molecular weight.

Thus, if a fragment Fab or Fab' is used as the starting antibody P, the value of m can vary between 0.3 and about 2; if a fragment $F(ab')_2$ is used, m can vary between 0.5 and about 4; for an antibody of the IgG type, the value of m will be between 0.5 and about 6; finally, for an antibody IgM, the value of m can vary between 1 and about 12.

It is preferable, however, for the degree of substitution on the antibody P to be such as to lead to a value of m which is not less than 0.5 and not more than 10.

More generally, the structures I and II above represent statistical formulae written in simplified form, as explained above.

Analogously, the formula IV, V and IX below are also statistical formula— whenever n is 1 because the coupling reactants are prepared from populations of proteins $P_1$ and $P_2$ which all have exactly the same properties as those considered above for the antibody P, whether these proteins $P_1$ and $P_2$ are themselves the antibody P or the protein GPIR-1a.

According to another feature, the present invention relates to a process for the preparation of a prolonged-action immunotoxin having a covalent bond of the disulfide or thioether type between an antibody and a glycoprotein which inactivates ribosomes, wherein a disulfide or thioether bond is formed between an antibody and a prolonged-action glycoprotein which inactivates ribosomes, obtained by treatment of a glycoprotein which inactivates ribosomes, the thiol groups of which are optionally protected, with an aqueous solution of an alkali metal periodate, for a period of 0.2 to 24 hours, at a temperature of 0° to 15° C. and in the absence of light, and by unblocking of the thiol group, if appropriate.

According to a preferred feature, the present invention relates to a process for the preparation of an immunotoxin having the structure I above, wherein a protein $P_1$, which is arbitrarily either the prolonged-action glycoprotein which inactivates ribosomes, GPIR-1a, or an antibody or antibody fragment, carrying at least one free thiol group attached to the said protein $P_1$ directly or via a spacing structure, is reacted, in aqueous solution and at room temperature, with a protein $P_2$, which is different from $P_1$ and is arbitrarily either the prolonged-action glycoprotein which inactivates ribosomes, GPIR-1a, or an antibody or antibody fragment, carrying a group capable of coupling with the free thiol of the protein $P_1$, so as to form a thioether or di-sulfide bond.

According to a particularly advantageous feature, the present invention relates to a process for the preparation of an immunotoxin having the structure II, in which P', W' and GPIR-1a are as defined above, wherein a protein of the formula:

$$P_{1'}—(Z—Y—E)_n—SH$$

is reacted, in aqueous solution and at room temperature, with a protein of the statistical formula:

$$P_{2'}—Z'—Y'—E'—G$$

in which $P_{1'}$, and $P_{2'}$ represent the radicals of the proteins $P_1$ and $P_2$ bonded to the groups belonging to the said proteins, or, only if $P_1$ and $P_2$ are an antibody or antibody fraction, the radicals of the proteins $P_1$ and $P_2$ originating from the opening of the carbohydrate structure by reaction with periodic acid, Z, Z', Y, Y', E and E' are as defined above and G represents a group:

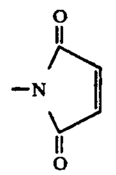

or a group —S—S—X, in which X is an activating group,

Therefore, both P and GPIR-la are proteins which arbitrarily have:

(1) the thiol group or groups taking part in the coupling, and (2) one or more functional groups capable of reacting with the above thiol groups to form a disulfide or thioether bond.

According to the present invention, the said thiol groups and functional groups are those of the native proteins P or GPIR-la or alternatively are introduced therein artificially.

The glycoproteins which inactivate ribosomes and which are used as starting materials for oxidation with periodate, according to the invention, are all GPIRs, such as the A chain of ricin, which are in themselves only very slightly cytotoxic because then cannot fix to cells, but which, on the other hand, after coupling with an antibody recognizing particular cells, become highly cytotoxic towards these cells once the antibody has recognized its target.

Representative starting compounds are the A chain of ricin, gelonine and the substance extracted from *Momordica charantia* (MOM), as obtained by extraction.

Other GPIRs which are useful as starting materials for oxidation with periodate ions are as follows:

| List | |
|---|---|
| Dianthin 30 | from *Dianthus caryophyllus* |
| Dianthin 32 | from *Dianthus caryophyllus* |
| Agrostin A | from *Agrostemma githago* |
| Agrostin B | from *Agrostemma githago* |
| Agrostin C | from *Agrostemma githago* |
| HCI | from *Hura crepitans* |
| *Asparagus officinalis* inhibitor | from *Asparagus officinalis* |

The same substances produced biosynthetically by cells whose genotype has been modified for this purpose are also suitable compounds.

Fragments of the above GPIRs, provided they retain all or part of the property of inactivating ribosomes which characterizes the GPIR from which they are derived, can also be used as starting materials.

The native A chain of ricin in which at least one of the thiol groups is protected is a preferred starting compound.

The preparation of the pure A chain of ricin is described in U.S. Pat. No. 4,340,535. Gelonine and MOM are also described.

Protection of the thiol groups of the starting GPIRs is only necessary if the said thiol groups are those which are to be used for coupling with the antibody. If other functional groups are used for the coupling, for example the phenolic hydroxyl of the tyrosines, protection is not carried out.

Blocking is carried out by reaction with a reagent capable of substituting the SH groups with a radical which can subsequently be removed by reduction or thiol/disulfide exchange, for example 2,2'-dinitro-5,5'-dithiodibenzoic acid (DTNB) or alternatively 3-(pyridin-2-yldisulfanyl)propionic acid. In the absence of such a treatment, the free thiols of the A chain may disappear during the oxidation reaction, in which case they cannot be totally regenerated by reaction with a reducing agent such as 2-mercaptoethanol. The excess blocking agent is removed by dialysis.

The glycoprotein which inactivates ribosomes and the thiols of which are blocked is then subjected to oxidation with periodate ions. If, on the other hand, the cytotoxic sub-unit does not contain thiol, or alternatively if the thiol or thiols are not used for coupling, the blocking indicated above is not carried out.

The periodate oxidation reaction is carried out at an acid pH of between 3 and 7, preferably of between 5 and 6.5. The periodate is used in excess; more particularly, the concentration of alkali metal periodate is greater than the concentration of the vicinal diols capable of being oxidized; concentrations of 10 to 50 mM in respect of sodium periodate for concentrations of 1 to 10 mg/ml of cytotoxic sub-unit are suitable. The treatment, carried out at a temperature of between 0° and 15° C., preferably of between 1° and 5° C., and in the dark, takes between 0.2 and 24 hours.

The reaction is stopped by the addition of a reagent which consumes the remaining periodate, for example an excess of ethylene glycol, and the by-products are removed by dialysis. The product obtained at the end of the reaction is isolated by the conventional techniques.

If the thiol groups of the starting material have been blocked, unblocking is effected by the known methods, for example by reaction with a reducing agent capable of freeing the previously blocked thiol group, such as 2-mercaptoethanol, giving the new prolonged-action glycoprotein which inactivates ribosomes, ready to be used for coupling with an antibody to give an immunotoxin.

In the case of the A chain of ricin, the new molecule obtained in this way (referred to by the symbols A-la) possesses the following main properties:

a molecular weight which is not significantly different from that of the native A chain. As far as it if possible to see by polyacrylamide gradient electrophoresis, this modification only produces polymers of the protein in a very small quantity and does not produce any degradation products.

a proportion of free thiol groups greater than 0.7 per mol.

an immunoreactivity towards rabbit antibodies directed against the A chain of ricin which is indistinguishable from that of the native A chain.

an inhibitory activity on protein synthesis in an acellular model which is greater than 50% of that caused by an equal quantity of native A chain.

finally, after a single intravenous administration to rabbits at a dose of about 0.4 mg/kg of body weight, the plasma level of the prolonged-action A chain (A-la) present in the bloodstream 23 hours after injection is greater than 10%of the level present at time zero (as against 0.015% for the native A chain at this time, i.e. an increase in the plasma level by a factor very much greater than 500).

Likewise, int he case of gelonine, the molecule obtained by periodate oxidation possesses the following main properties:

a molecular weight which is not significantly different from that of the native gelonine.

an immunoreactivity towards anti-gelonine rabbit antibodies which is indistinguishable from that of the native gelonine.

finally, after a single intravenous administration to rabbits at a dose of about 0.3 mg/kg of body weight, the plasma level of the modified gelonine 24 hours after injection is greater than 3% of the level present at time zero (as against 0.01% for the native gelonine at this time, i.e. an increase in the plasma level by a factor greater than 200).

The preparation of the conjugates or immunotoxins from the prolonged-action glycoproteins which inactivate ribosomes is carried out by any process suitably chosen from the range of processes described in U.S. Pat. No. 4,340,535. If the chosen cytotoxic sub-unit naturally contains at least one thiol making it suitable for coupling, this group will preferably be used by reaction with the antibody or antibody fragment carrying an activated disulfide group. If the chosen cytotoxic sub-unit does not naturally possess a thiol group making it suitable for coupling, at least one functional group carrying a free thiol can preferably be introduced artificially into the said sub-unit, after the oxidation step with periodate ions, by any known process and the coupling can be continued as indicated above.

The introduction of the said functional group can take place either before the oxidation step with periodate ions, in which case it will be necessary for the thiol radical to be blocked during the oxidation step and then unblocked after this step, or after the oxidation step.

The preparation of monoclonal antibodies directed against human cancer cells has been widely reported in the scientific literature and many of these antibodies are now commercially available.

In the process of the present invention, the chemical coupling of the GPIR-1a with the antibody (or antibody fragment) can be effected by procedures which:

preserve the respective biological activities of the two components of the conjugate, namely the antibody and the GPIR-1a, ensure that the process has a satisfactory reproducibility and a good coupling yield, make it possible to control the value of the ratio GPIR-1a/antibody in the conjugate obtained, and lead to a stable and water-soluble product.

Among the procedures corresponding to these characteristics, preference must be given to those which involve one or more thiol groups in forming the bond between the 2 proteins. In fact, these thiol groups are particularly suitable for forming either disulfide bonds or thioether bonds, both of which satisfy the general conditions above.

The preparation of immunotoxins simultaneously having the following characteristics:

the covalent bond between the A chain of ricin and the antibody contains a disulfide radical, one of the sulfur atoms forming the disulfide bond is always the sulfur atom belonging to the cysteine residue in the 257-position of the A chain of ricin, and the link joining the A chain of ricin to the antibody is fixed to the latter at $NH_2$ side groups or end groups of a peptide chain, and formed by the coupling of an antibody with the A chain of ricin as described in detail in U.S. Pat. No. 4,340,535.

The same method can be applied to the preparation of immunotoxins having the same characteristics and formed by the coupling of an antibody or antibody fragment with a GPIR-1a.

The preparation of immunotoxins formed by the coupling of an antibody or antibody fragment with a GPIR-1a and by covalent bond of the disulfide or thioether type at different functional groups is described in detail below.

In general, in order to carry out the coupling reactions between proteins successfully and to eliminate disordered crosslinkings in particular, it is important for one of the proteins to be coupled, and one only, to carry the thiol or thiol groups to be used, while the other protein only carries one or more groups capable of reacting with the thiols in an aqueous medium having a pH of between 5 and 9, and at a temperature not exceeding 30° C., to produce a stable and clearly defined covalent bond.

DESCRIPTION OF THE PREFERRED EMBODIMENTS

Figure 1:
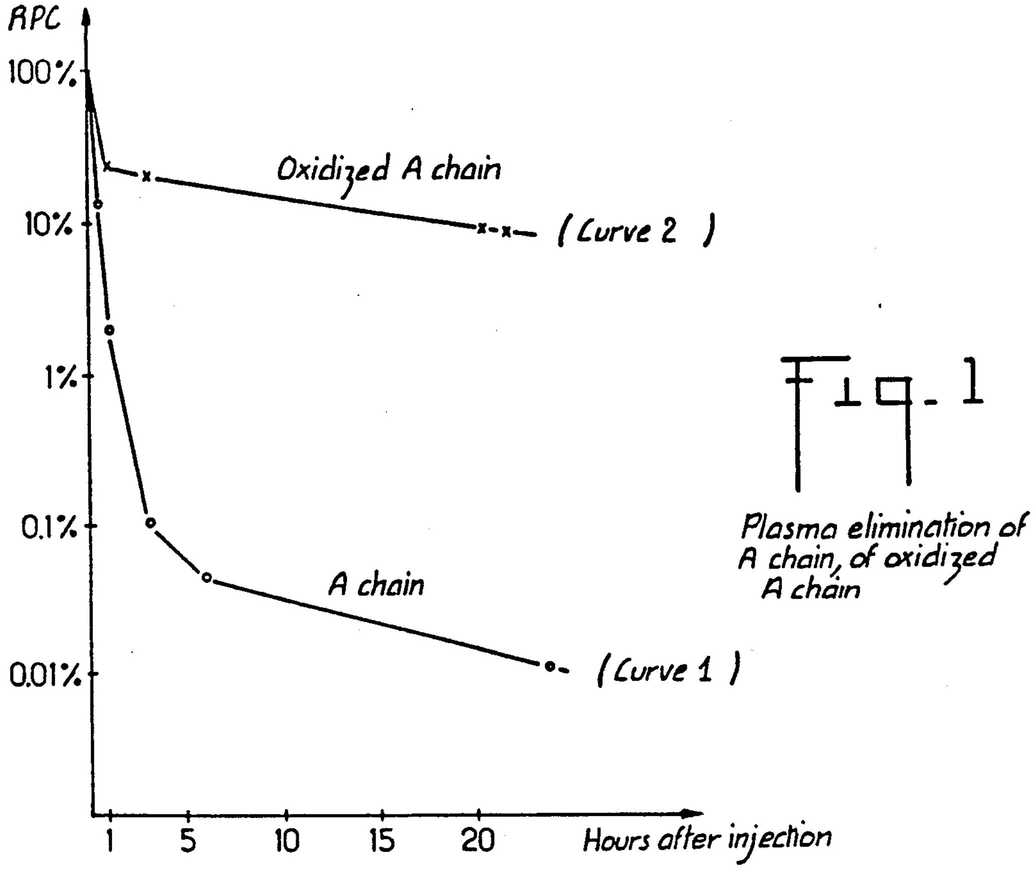
FIG. 1 shows the plasma elimination curves of the A chain and of the oxidized A chain of ricin.

The characteristics of the proteins $P_1$ and $P_2$ used as starting materials are illustrated in detail below. The spacing structure E can be replaced with the preferred structures R to $R_8$, which are only given as examples.

I—THE PROTEIN $P_1$

As this protein is in all cases the one carrying the thiol group or groups which will take part in the coupling, the situation which arises varies according to the nature of this protein $P_1$.

A) In the natural state, the protein $P_1$ carries one or more thiol radicals which can be used to permit coupling with the protein $P_2$; this is particularly the case if the protein $P_1$ is the antibody fragment known as F(ab)', as conventionally obtained by limited proteolysis of the antibody in the presence of pepsin, followed by reduction of the disulfide bridge (or bridges) between high-molecular chains.

This is also the case if the protein $P_1$ is a GPIR-1a, for example the modified A chain of ricin (A-1a), or a derivative thereof, in which at least one of the thiol groups carried by the cysteine 171 and 257 residues of the native A chain of ricin is free and accessible for chemical coupling.

In all these cases, the protein $P_1$ carrying its natural thiol group (or groups) can be used in this state for the coupling step.

B) In the natural state, the protein $P_1$ does not carry thiol radicals which can be used to permit coupling with the protein $P_2$:

this is especially the case if the protein $P_1$ is a native immunoglobulin, a whole antibody or an antibody fragment, especially one of the fragments conventionally called $F(ab)'_2$ or F(ab);

another case in which the protein $P_1$ does not carry, in the natural state, a thiol group which can be used for coupling is the case where this protein $P_1$ is a GPIR-1a, for example the prolonged-action A chain of ricin, in which each of the two cysteine residues is either blocked by alkylation or inaccessible for chemical modification.

In all cases, it will thus be appropriate artificially to introduce into such molecules one or more thiol groups capable of permitting coupling.

Three types of reaction can preferably be used for the introduction of thiol groups:

1—The first type of reaction is with S-acetylmercaptosuccinic anhydride, which is capable of acylating amino groups of the protein. It will then be possible to free the thiol groups by reaction with hydroxylamine to remove the acetyl protecting radical, in the manner already described (Archives of Biochemistry and Biophysics, 119, 41–49, 1967). It will even be possible, in the case where the thiol group (or groups) thus introduced in the protected form are subsequently to react with an activated mixed disulfide radical, to dispense with the prior deprotection by means of hydroxyalmine; in fact, the reaction creating the disulfide bond using the reactants forming the subject of the present invention takes place just as well with the S-acetyl radical as with the free thiol.

Other methods described in the scientific literature can also be used to introduce thiol groups into the protein to be modified.

2—The second type of reaction consists in reacting the protein via its carboxyl groups with a symmetrical diamino molecule having a disulfide bridge, of the formula:

$$H_2N—R_1—S—S—R_1-NH_2$$

in which $R_1$ is an aliphatic group containing from 2 to 5 carbon atoms.

The reaction is preferably carried out with cystamine $[R_1 = —(CH_2)_2—]$ in the presence of a coupling agent such as a carbodiimide and especially a water-soluble derivative like 1-ethyl-3-dimethylaminopropyl-3-carbodiimide, and leads to the formation, depending on the stoichiometries used, of one of the following derivatives or a mixture of both:

$$P_{1'}—CO—NH—R_1—S—S—R_1—NH_2 \quad (Ia)$$

$$P_{1'}—CO—NH—R_1—S—S—R_1—NH—CO—P_1 \quad (Ib).$$

A reaction product of this type can then be used in two ways:

a) If, in the formulae Ia or Ib, the protein $P_1$ is a GPIR-1a, for example the prolonged-action A chain of ricin or one of its derivatives, the reaction medium obtained is subjected, without fractionation, to the action of a reducing agent such as 2-mercaptoethanol, giving a single protein derivative of the general formula:

$$P_{1'}—CONH—R_1—SH.$$

The product thus obtained is then purified by dialysis or gel filtration.

b) If, in the formulae Ia and Ib, the protein $P_1$ is an antibody or one of its fragments, the reaction medium obtained will be used as such for the coupling, in which case a thiol/disulfide exchange method will be used, for example the one described by Gilliland and Collier (Cancer Research, 40, 3564, 1980).

3—The third type of reaction consists in using carbohydrate units, which are present in the natural state in the antibodies, in order to fix the radical carrying the thiol which it is proposed to introduce. The protein P is then subjected to oxidation with periodate ions by the known methods in order to create aldehyde groups on the carbohydrate units. After the reaction has been stopped by the addition of excess ethylene glycol and the by-products and excess reactants have been removed by dialysis, the product obtained is treated with a symmetrical diamino molecule having a disulfide bridge, of the general formula:

$$H_2N—R_1—S—S—R_1—NH_2$$

in which $R_1$ is an aliphatic group containing from 2 to 5 carbon atoms. The addition products formed are then reduced to secondary or tertiary amines by reaction with a suitable metal hydride, especially sodium borohydride. The reaction is preferably carried out with cystamine $[R_1 = —(CH_2)_2—]$ and leads to the formation, depending on the stoichiometries used, of one of the following derivatives or a mixture of both:

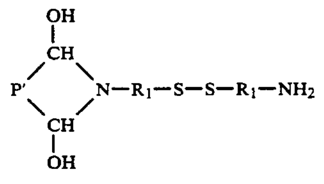
IIa

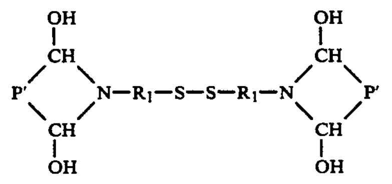
IIb

The reaction medium obtained may then be treated exactly as indicated above for the products characterized by the structures Ia or Ib.

In the last two types of reaction, described above, for the artificial introduction of thiol groups (the types using a symmetrical diamino disulfide reactant), the protein $P_1$ used preferably possesses neither free SH groups nor free amino groups.

In the case of the GPIR-1a, this can always be achieved by alkylation of the natural SH group or groups by reaction with a customary reagent for thiols, such as N-ethylmaleimide or iodoacetic acid or one of its derivatives, and by methylation of the natural $NH_2$ groups in accordance with the reductive methylation process described in MEANS and FEENEY (Biochemistry 7, 2191 (1968)). For example, up to 6 methyl radicals per mol can be introduced beforehand into the modified native A chain of ricin. A protein of this type retains all its biological properties and especially its capacity to inhibit ribosomal protein synthesis in eucaryotic cells.

In the cases of antibodies or antibody fragments and, more generally, all the substances of the first group, as defined previously, which do not posses naturally free SH groups, it will be appropriate to carry out a reductive methylation, for example by the method of MEANS and FEENEY; in this way, it is usually possible to introduce several dozen methyl radicals per mol of antibody without modifying its capacity to selectively recognize an antigen on the surface of the cells carrying this antigen.

II—THE PROTEIN $P_2$

This protein is in all cases the one which carries one or more functional groups capable of reacting with the thiols of the protein $P_1$ to form either a disulfide or a thioether bond. These functional groups, which are always introduced artificially into the protein $P_2$, differ according to whether it is desired to effect coupling by a disulfide bond or by a thioether bond and are chosen as indicated below.

1) The disulfide bond

In this case, the preparation of the conjugate can be represented by the equation:

$$P_{1'}—(Z—Y—E)_n—SH+P_{2'}—Z'—Y'—E'—S—S—X \rightarrow P_{1'}—(Z—Y—E)_n—S—S—E'—Y'—Z'—P_{2'}+X—SH$$

The protein $P_2$ substituted by an activated sulfur atom is obtained from the protein $P_2$ itself or from the correctly protected protein $P_2$ by substitution with a reagent which itself carries an activated sulfur atom, according to the equation:

$$P_2+L—Y'—R—S—S—X \rightarrow P_{2'}—Z'—Y'—R'—S—S—X$$

in which:

$P_2$ denotes the protein to be substituted and

L—Y' represents a group permitting the covalent fixation of the reagent to the protein.

The functional group L—Y' is a group capable of bonding covalently with any one of the groups carried by the side chains of the constituent amino acids of the protein to be substituted. Among these groups, the following may be singled out in particular:

a) The amino end groups of the peptide chains or the amino side groups of the lysyl radicals contained in the protein. In this case, L—Y' can represent especially:

a carboxyl group which can bond to the amino groups of the protein in the presence of a coupling agent such as a carbodiimide and especially a water-soluble derivative like 1-ethyl-3-dimethylaminopropyl-3-carbodiimide;

a carboxylic acid chloride which is capable of reacting directly with the amino groups to acylate them;

a so-called "activated" ester such as an ortho- or para-nitrophenyl or -dinitrophenyl ester, or alternatively an N-hydroxysuccinimide ester, which can react directly with the amino groups to acylate them;

an internal anhydride of a dicarboxylic acid, such as, for example, succinic anhydride, which reacts spontaneously with the amine groups to create amide bonds; or an imidoester group:

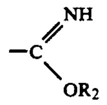

(L = $OR_2$, Y' = —(C=NH)—)

in which R is an alkyl group, which reacts with the amino groups of the protein $P_2$ according to the equation:

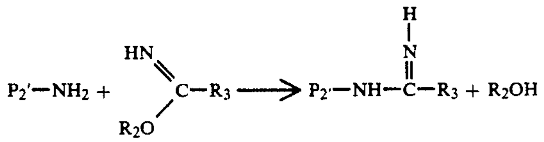

in which $R_3$ represents the group —R—S—SX;

b) the phenol groups of the tyrosyl radicals contained in the protein. In this case, L—Y' can represent especially an imidazol-1-ylcarbonyl group, which reacts with the phenol groups of the protein according to the equation:

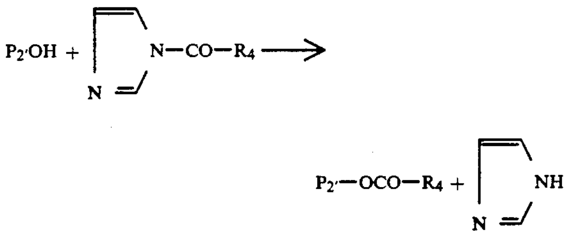

in which the imidazol-1-yl is L, the CO group is Y' and $R_4$ is the group —R—S—S—X.

The radical —S—S—X denotes an activated mixed disulfide capable of reacting with a free thiol radical. In particular, in this mixed disulfide, X can denote a pyridin-2-yl or pyridin-4-yl group optionally substituted by one or more alkyl, halogen or carboxyl radicals. X can also denote a phenyl group preferably substituted by one or more nitro or carboxyl groups. Alternatively, X can represent an alkoxycarbonyl group such as the methoxycarbonyl group.

The radical R denotes the spacing structure (indicated as E in the general formula II above) capable of carrying the substituents Y' and S—S—X simultaneously. It must be chosen so as not to contain groups capable of interfering, during the subsequent reactions, with the reactants used and the products synthesized. In particular, the group R can be a group $-(CH_2)_n-$, n being between 1 and 10, or alternatively a group:

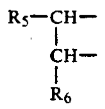

in which $R_6$ denotes hydrogen or an alkyl group having from 1 to 8 carbon atoms and $R_5$ denotes a substituent which is inert towards the reactants to be used subsequently, such as a carbamate group:

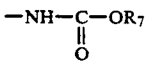

in which $R_7$ denotes a linear or branched alkyl group having from 1 to 5 carbon atoms, especially the tert.-butyl group. The reaction of the compound L—Y'—R—S—S—X with the protein $P_2$ is carried out in a homogeneous liquid phase, most commonly in water or a buffer solution. If necessitated by the solubility of the reactants, a water-miscible organic solvent can be added to the reaction medium at a final concentration which can reach 20% by volume in the case of a tertiary alcohol, such as tertiary butanol, or 10% by volume in the case of dimethylformamide or tetrahydrofuran.

The reaction is carried out at room temperature for a period of time varying from a few minutes to a few hours, after which the low molecular weight products, and in particular the excess reactants, can be removed by dialysis or gel filtration. This process usually makes it possible to introduce between 1 and 15 substituent groups per mol of protein.

When using such compounds, the coupling with the protein $P_1$ is carried out by brining the two proteins together in an aqueous solution having a pH of between 6 and 8, at a temperature not exceeding 30° C., for a period of time varying from 1 hour to 24 hours. The aqueous solution obtained is dialyzed, if appropriate, to remove the low molecular weight products, and the conjugate can then be purified by a variety of known methods.

2) The thioether bond

In this case, the preparation of the conjugate consists in reacting $P_{1'}$—(Z—Y—E)$_n$—SH with the protein $P_2$ into which one or more maleimide radicals have been introduced beforehand.

The reaction is then represented by the following equation, which is given as an example:

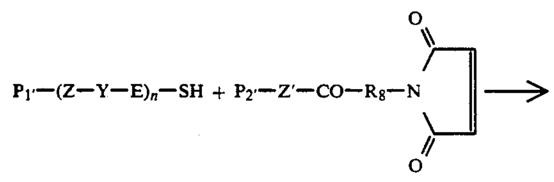

-continued

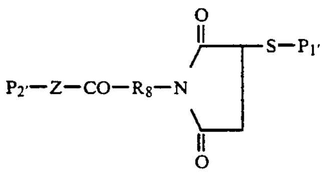

in which:

$R_8$ represents an aliphatic or aromatic spacing structure containing from 1 to 15 carbon atoms, which is inert towards the reactants to be used subsequently, and Z represents groups which can vary according to the type of functional group substituted on the protein $P_2$.

Thus, Z=oxygen in the case of an ester on the phenol of a tyrosyl residue, Z=NH in the case of the coupling of an activated carboxyl group with an amino group of the protein, or Z=NH—$CH_2$ in the case of the reaction of a chloromethyl ketone with an amino group of the protein.

The protein $P_2$ substituted by the maleimide group or groups is obtained from the protein $P_2$ itself, or the correctly protected protein $P_2$, by substitution of suitable groups of the protein with a reagent which itself carries the maleimide group. Among these suitable groups, the following may be singled out in particular:

a) The amino end groups of the peptide chains or the amino side groups of the lysyl residues contained in the protein. In this case, the reagent carrying the maleimide radical can be:

either a reagent of the general formula:

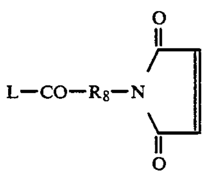

in which L—CO— represents:

either a carboxyl group, in which case the reaction is carried out, after activation of the carboxyl group, in the presence of a coupling agent such as a carbodiimide and especially a water-soluble derivative such as 1-ethyl-3-dimethylaminopropyl-3-carbodiimide, or a so-called "activated" ester such as an ortho- or para-nitrophenyl or -dinitrophenyl ester, or alternatively an N-hydroxysuccinimide ester, which reacts directly with the amino groups to acylate them.

The preparation of such reagents is described especially in Helvetica Chimica Acta 58, 531-541 (1975). Other reagents in the same class are commercially available.

or a reagent of the general formula:

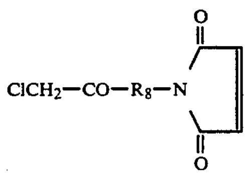

which is capable of reacting with the amino groups of the protein $P_2$ according to the equation:

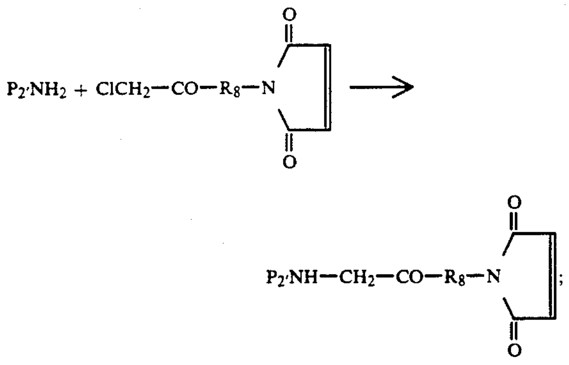

b) the phenol groups of the tyrosyl radicals contained in the protein. In this case, the reagent carrying the maleimide radical can be a reagent of the general formula:

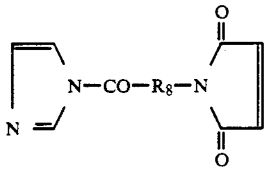

which reacts with the phenol groups of the protein according to the equation:

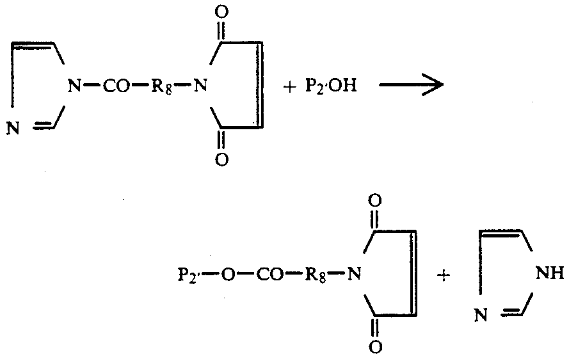

The reaction of the maleimide-carrying reagents with the protein $P_2$ is carried out in a homogeneous liquid phase, most commonly in water or a buffer solution. If necessitated by the solubility of the reactants, a water-miscible organic solvent can be added to the reaction medium at a final concentration which can reach 20% by volume in the case of a tertiary alcohol, such as tertiary butanol, or 10% by volume in the case of dimethylformamide or tetrahydrofuran.

The reaction is carried out at room temperature for a period of time varying from a few minutes to a few hours, after which the low molecular weight products, and in particular the excess reactants, can be removed by dialysis or gel filtration. This process usually makes it possible to introduce between 1 and 15 substituent groups per mol of protein.

When using such compounds, the coupling with the protein $P_1$ is carried out by bringing the two proteins together in an aqueous solution having a pH of between 6 and 8, at a temperature not exceeding 30° C., for a period of time varying from 1 hour to 24 hours. The solution obtained is dialyzed, if appropriate, to remove the low molecular weight products, and the conjugate can then be purified by a variety of known methods.

The compounds of the formula:

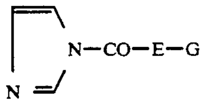

VI in which E and G are as defined above, are prepared by a process which comprises reacting a compound of the formula:

G—E—COOH VII in which G and E are as defined above, with the carbonyldiimidazole of the formula:

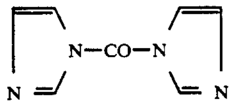

VIII in an organic solvent at a temperature of 10° to 40° C.

The compounds of the formula VI are particularly useful as agents for coupling with the hydroxyls of the tyrosines of the proteins GPIR-1a and P.

According to another feature, the present invention relates to new products having the following statistical formula:

GPIR-1a"—O—CO—E—G IX in which:

GPIR-1a" represents the radical of the protein GPIR-1a or any molecule derived from the said GPIR-1a by artificial modification of any one of its functional groups, from which one or more phenolic hydroxyl groups of the tyrosines have been removed;

the oxygen atom is that belonging to the phenolic hydroxyl groups missing from the radical GPIR-1a"; and E and G are as defined above.

Particular preference is given to the compounds of the formula IX in which E represents a group $-(CH_2)_p-$, in which p is an integer from 2 to 7, or a group:

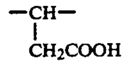

and G is a group of the structure —S—S—X, in which X is an activating radical chosen from the pyridin-2-yl and pyridin-4-yl groups which are unsubstituted or substituted by one or more halogens or alkyl, carboxyl or alkoxycarbonyl radicals, the phenyl group which is unsubstituted or substituted by one or more halogens or nitro, alkoxy, carboxyl or alkoxycarbonyl groups, or an alkoxycarbonyl group.

The products of the formula IX are prepared by reacting a product of the formula:

GPIR-1a"-OH in which GPIR-1a" is as defined above and the hydroxyl group is the phenolic hydroxyl missing from the tyrosines of the radical GPIR-1a", with a compound of the formula VI above, at a temperature of 10° to 40° C., in an aqueous solvent optionally containing a water-miscible organic solvent such as, for example, an ether solvent like dioxane or tetrahydrofuran.

In the case where GPIR-1a is the prolonged-action A chain of ricin, the properties of the resulting immunotoxins IT (A-1a) are as follows:

the average degree of coupling, expressed as the number of mol of modified A chain per mol of antibody, is usually between 0.5 and 5 and in particular between 1 and 3, the separation of the IT (A-1a) by polyacrylamide gel electrophoresis results in a splitting of the product into a series of bands corresponding to products whose molecular weights differ from that of the antibody by successive increments of 30,000 daltons, the studies performed by cytofluorometry make it possible to show that the antibody has not undergone any substantial degradation during the activation and coupling reactions to which it has been subjected, and that it is still capable, within the conjugate itself, of recognizing the antigen against which it is directed, and the inhibitory activity of the A chain, modified and coupled with an antibody, on protein synthesis, determined in an acellular model in the presence of 2-mercaptoethanol, is totally retained.

The cytotoxic activity of the immunotoxins IT (A-1a), measured in the presence of an activator in a test for protein synthesis in a cell model on the cells having the target antigen, is more than 1000 times greater than that measured under the same conditions on cells not having the target antigen. For example, the immunotoxin (denoted by IT (A-1a) (T101) built up by coupling the modified A chain of ricin, by means of a link containing a disulfide bridge, with a monoclonal antibody (denoted by antibody T101) directed against the antigen T65 present on the surface of certain human leukemia cells is about $10^5$ times more cytotoxic towards the positive T65 cells than towards the negative T65 cells, the cytotoxic efficacy of the immunotoxins IT (A-1a), measured by the clonogenic test, is as high as that obtained with the corresponding conventional ITs. For example, IT (A-1a) T101 at a dose as low as $10^{-11}$ M, in the presence of 10 mM ammonium chloride, leads to a specific cytoreduction of the order of 99.999% of the initial value. This result is identical to those obtained with IT T101, built up with the same antibody and the unmodified A chain of ricin, and finally, after intravenous administration of IT (A-1a) to rabbits at a dose of the order of 0.4 mg/kg of body weight, expressed as A chain, the plasma level of IT (A-1a) present in the bloodstream 23 hours after injection is 10 to 200 times greater than the plasma level of the conventional IT measured under the same conditions. Thus, in a typical case involving rabbits, it is found that the plasma level of IT (A-1a) T101 in the bloodstream 23 hours after injection is 7% of the product present at time zero, as against 0.05% for the corresponding conventional IT T101 after the same time, i.e. an increase by a factor of the order of 140.

This gives modified immunotoxins which have acquired a new character as regards their pharmacokinetic properties.

More particularly, by appropriate modification of the cytotoxic sub-unit, it has been possible to add to the specific cytotoxicity properties of immunotoxins, without interfering with them, a new property which is just as intrinsic, namely the capacity to show slow plasma elimination kinetics.

The examples which follow provide a clearer understanding of the invention without limiting its scope.

EXAMPLE 1

This example demonstrates the slow elimination of the A chain of ricin modified with sodium periodate, after intravenous injection into the animal.

Modification of the A chain of ricin with sodium periodate

1) Blocking of the natural SH with DTNB

The A chain of ricin was prepared and purified in the manner indicated in U.S. Pat. No. 4,340,535. 20 equivalents of a solution of 2,2'-dinitro-5,5'-dithiodibenzoic acid (DTNB), i.e. 385 microliters of a 0.1M solution of DTNB in a 125 mM phosphate buffer of pH 7 (this solution is brought to pH 7 with sodium hydroxide), are added to 10 ml of a solution of A chain of ricin containing 5.6 ,g/ml (with 0.84 thiol group per A chain) in PBS buffer (a buffer 20 mM in respect of phosphate and 150 mM in respect of NaCl, of pH 7). Incubation is left to proceed for 20 minutes at 20° C. The solution is then dialyzed against PBS buffer at 4° C. to give 53 mg of A chain blocked on the thiol group, as a solution containing 5 mg/ml.

2) Periodate oxidation of the blocked A chain 120 microliters of a 0.5M solution of sodium periodate in water are added to 6 ml of a solution containing 5 mg/ml of blocked A chain, brought to pH 6 with 1M acetic acid. Incubation is left to proceed for 16 hours at 4° C. in the dark. The oxidation reaction is stopped by the addition of 620 microliters of a 1M aqueous solution of ethylene glycol. After incubation for 15 minutes at 20° C., the reaction medium is dialyzed at 4° C. against PBS buffer. The periodate oxidation produces a slight precipitate of protein, which is removed by centrifugation at 10,000×g for 30 minutes. This gives 24 mg of oxidized blocked A chain at a concentration of 3.4 mg/ml.

3) Unblocking of the thiol groups

2-Mercaptoethanol is added as a reducing agent, at a final concentration of 1%, to 6 ml of oxidized blocked A chain containing 3.4 mg/ml in PBS buffer. Incubation is left to proceed for 1 hour at 20° C. The solution is then dialyzed against PBS buffer at 4° C. This given 19 mg of oxidized A chain at a concentration of 2.8 mg/ml.

Using the DTNB technique (Methods in Enzymology, 1972, 25, 457 (Academic Press)), it is determined that the modified A chain obtained has 0.70 free thiol group per mol. The molecular weight of the modified A chain is 30,000±3,000, determined by polyacrylamide gradient electrophoresis in the presence of sodium dodecylsulfate.

The previously obtained preparation of A chain in which the polysaccharide units have been oxidized was studied for its enzymatic activities in the inhibition of protein synthesis and for its pharmacokinetic properties.

II—Enzymatic activity of the prolonged-action A chain, measured on an acellular model The fundamental biological property of the A chain of ricin is to inhibit protein synthesis in cells by degradation of the ribosomal sub-unit 60S.

The in vitro protocol involves the use of appropriately complemented, subcellular fractions of rat liver capable of incorporating $^{14}$C-phenylalanine in the presence of an artificial messenger RNA: polyuridylic acid.

The procedure employed for preparing the subcellular fractions and measuring the incorporation of $^{14}$C-phenylalanine is an adaptation of the method described in Biochemica Biophysica Acta 1973, 312, 608-616, using both a microsomal fraction and a cytosol fraction of the rat hepatocytes. The sample containing the A chain is introduced in the form of a solution appropriately diluted in a 50 mM Tris HCl buffer of pH 7.6 containing 0.2% of 2-mercaptoethanol and 15 micrograms/ml of bovine serum albumin.

The count data are used to calculate, relative to a control medium without inhibitor, the percentage inhibition of the incorporation of $^{14}$C-phenylalanine into the proteins for each reaction medium containing A chain of ricin.

The inhibitory activity was determined. An $IC_{50}$ of $7.8 \cdot 10^{-9}$ mol/l is observed for the oxidized A chain. The $IC_{50}$ of the control A chain in the experiment is $13 \cdot 10^{-9}$ mol/l; therefore, the modification does not cause a loss of activity of the A chain.

III—Pharmacokinetic properties of the prolonged-action A chain modified on its polysaccharide units The A chain is administered to rabbits by means of a single injection into a vein in the ear. The quantity of A chain injected corresponds to 0.415 mg/kg. Blood samples are taken at intervals on heparin. The plasmas are analyzed with the aid of a radioimmunometric test designated below by the abbreviation RIM-1.

This technique has the advantage of determining the A chain without modifying it. This determination is carried out in microtitration plates (for example: "NUNC-TSP screening system" from Poly Labo Block France), the lid of which carries hyperabsorbent spikes which dip into the wells in the base. These spikes constitute the solid phases. Sheep antibodies directed against the A chain of ricin (designated below by the abbreviation Ac1), purified by affinity chromatography, are absorbed on the solid phases. For this purpose, 200 microliters of a solution of Ac1 containing 10 micrograms/ml in PBS phosphate buffer are divided up into the wells. The spikes are brought into contact firstly with the solution of Ac1 for 24 h at 4° C. and then with fetal calf serum for 3 h at 20° C. in order to saturate all the fixation sites. The saturated immunoabsorbent is then brought into contact for 3 h at 20° C. with the plasma samples to be determined at different dilutions, or with solutions of A chain of known concentrations in order to establish the calibration curve. After washing with a PBS buffer, the immunoabsorbent is brought into contact for 2 h at 20° C. with the sheep antibodies directed against the A chain of ricin, which have been purified by affinity chromatography and radiolabeled (designated below by the abbreviation Ac2). The radiolabeling of the Ac2 is effected with iodine 125 in the presence of chloramine T by the method of Greenwood and Hunter (Biochem. J., 1963, 89, 114); the specific activity of the radiolabeled Ac2 antibodies is 5 to 10 microcuries/microgram. $10^6$ cpm of radiolabeled AC2 antibodies are introduced as 200 microliters into a PBS buffer containing 0.1% of bovine serum albumin. After washing in PBS buffer, the spikes are detached and the quantity of bound Ac2 is measured by counting the radioactivity. The concentration of A chain in the samples to be determined is measured by reference to the calibration curve established by introducing the A chain at different known concentrations. When prolonged-action A chain is injected into the animal, this same prolonged-action A chain is used to establish the corresponding calibration curve.

The values of the concentration of A chain in the blood plasma measured by this technique are reproducible and reliable. The detection threshold is 1 nanogram/ml. A study of the reproducibility within and between experiments gives coefficients of variation of less than 10% for concentration values within the range from 1 to 200 nanograms/ml.

The results of these experiments are represented in the form of curves in which the time, expressed in hours, is plotted on the abscissa and the plasma concentration of the product measured, recorded in per cent of the theoretical plasma concentration at time zero, is plotted on a logarithmic scale on the ordinate. This value, called the "relative plasma concentration" (RPC) is calculated using the following expression:

$$RPC = \frac{\text{concentration measured at time } t}{\text{quantity injected/plasma volume}} \times 100$$

The plasma volume is considered to be equal to 36 ml/kg of the animal's body weight.

FIG. 1 shows the plasma elimination curve, as a function of time, for the native A chain of ricin injected intravenously. This curve (curve 1) has two phases: in the first phase, the product disappears very rapidly from the bloodstream since only 0.1% of the dose administered remains in the plasma three hours after injection. In the second phase, the decrease in slower.

When the A chain has been oxidized on its polysaccharide units, the elimination profile is profoundly modified: the first elimination phase—which is responsible for the disappearance of the majority of the product—is practically suppressed, which leads to a considerable increase in the plasma levels of A chain. Twenty hours after injection, the concentration of the oxidized A chain is 600 times greater than in the case of the unmodified A chain (curve 2).

EXAMPLE 2

This example demonstrates the importance of the duration of the oxidative treatment on the pharmacokinetic properties of the oxidized A chain.

Six preparations of oxidized A chain are made up using the procedure indicated in Example 1, except for the duration of the sodium periodate treatment. The treatment times are as follows: zero (reaction stopped immediately with ethylene glycol), 20 minutes, 40 minutes, 2.5 hours, 4 hours and 18 hours.

These various preparations are injected into rabbits and the relative plasma concentration of the A chain is measured after 23 hours by the same procedure as in Example 1.

Figure 2:
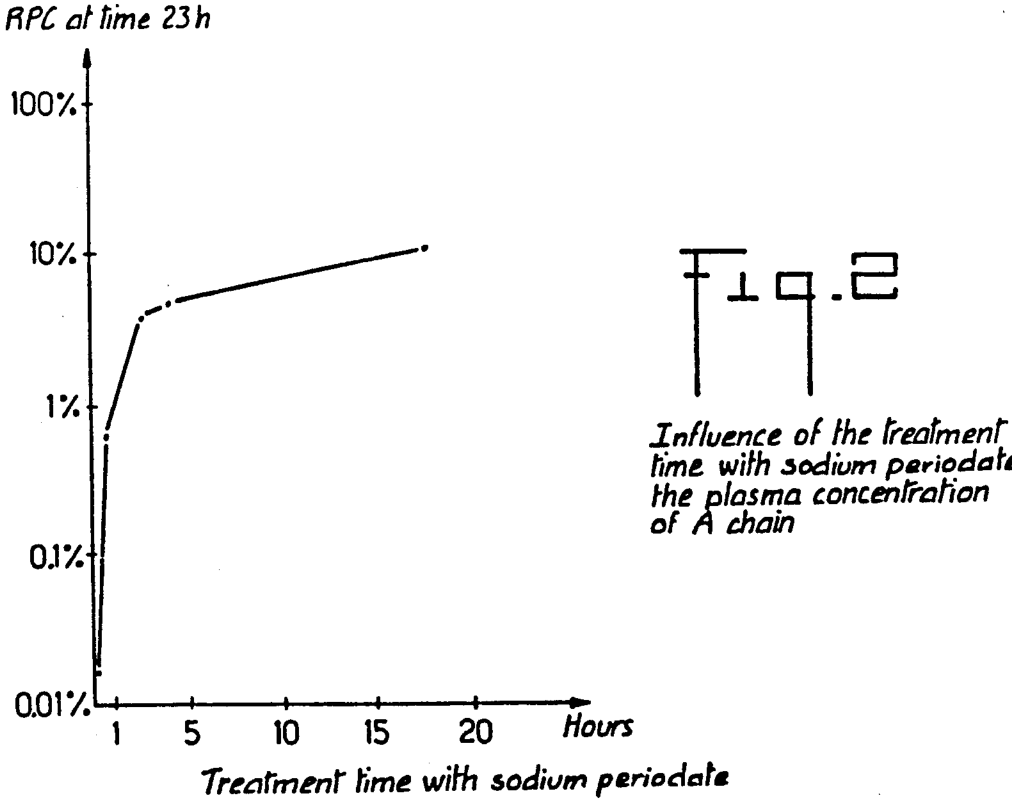
FIG. 2 shows the influence of the treatment time with sodium periodate on the plasma concentration of the A chain of ricin.

The results are shown in FIG. 2. These results indicate that 1) the increase in the plasma level of the A chain is indeed due to periodate oxidation because, when the reaction is stopped immediately, the plasma concentration of A chain is identical to that obtained for the native A chain, and 2) it is necessary for the duration of this reaction to be relatively long in order to obtain optimum effects.

EXAMPLE 3

This example demonstrates 1) the rapid elimination of native gelonine, and 2) the slow elimination of gelonine modified with sodium periodate, after intravenous injection into the animal.

I—Modification of gelonine with sodium periodate

The gelonine was prepared and purified from Gelonium multiflorum by the method which has been described (J. Biol. Chem. (1980) 255, 69047-6953). The oxidation reaction is carried out under the same conditions as those described for the A chain of ricin in Example 1, except that the step in which the thiols are blocked with DTNB is omitted.

In fact, as the coupling of gelonine with the antibody is not generally performed using natural thiol groups of the gelonine, the thiol groups will be introduced artificially, after the oxidation step, by the technique described in Cancer Res., 1984, 44, 129-133. 21 microliters of a 0.5 M solution of sodium periodate in water are added to 1 ml of a solution containing 3 mg/ml of gelonine in PBS buffer, brought to pH 6 with 1 M acetic acid. Incubation is left to proceed for 16 hours at 4° C. in the dark. The reaction is stopped by the addition of 105 microliters of a 1 M aqueous solution of ethylene glycol. After incubation for 15 minutes at 20° C., the reaction medium is dialyzed at 4° C. against PBS buffer. After centrifugation at 10,000×g for 30 minutes, this gives 2.9 mg of oxidized gelonine at a concentration of 2.5 mg/ml.

Like the A chain of ricin, the fundamental property of gelonine is to inhibit protein synthesis in eucaryotic cells by degradation of the ribosomal subunit 60S (Biochem. J., 1982, 207, 505-509). In the case of gelonine too, the modification due to periodate oxidation does not cause a loss of activity.

II—Pharmacokinetic properties of prolonged-action gelonine

Native gelonine or gelonine modified by the procedures explained above is administered to rabbits by a single injection into a vein in the ear. The quantity of gelonine injected is between 0.3 and 0.4 mg/kg. Blood samples are taken at intervals on heparin. The plasmas are analyzed with the aid of a radioimmunometric test designated below by the abbreviation RIM-2.

This assay is performed by the same technique as used for the test RIM-1, except that the solution Ac1 here is a solution of anti-gelonine rabbit antibodies purified by affinity chromatography, the AC2 antibodies being the same antibodies radiolabeled. The radiolabeling procedure is identical to that described for the technique RIM-1. The concentration of native gelonine or modified gelonine in the samples to be determined is measured by reference to a calibration curve established by introducing native or modified gelonine at different known concentrations. The assay RIM-2 has the same reliability and reproducibility characteristics as described for the technique RIM-1. The results of these experiments are represented in the same way as for the A chain of ricin in Example 1.

Figure 3:
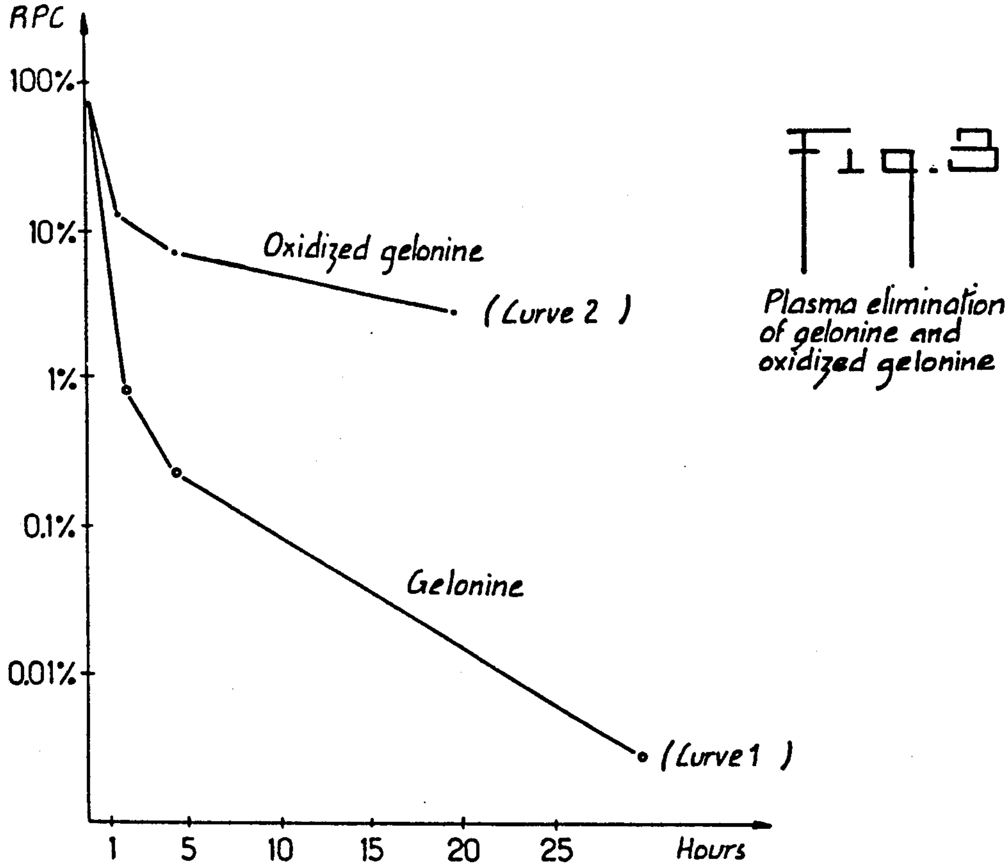
FIG. 3 shows the plasma elimination curves of gelonine and oxidized gelonine.

FIG. 3 shows the plasma elimination curves, as a function of time, for native gelonine and oxidized gelonine, injected intravenously. The native gelonine, like the native A chain of ricin, disappears very rapidly from the bloodstream since 99.99% of the gelonine present in the bloodstream disappears in 24 hours (curve 1). When the gelonine has been oxidized on its polysaccharide units, the elimination profile is profoundly modified: 24 hours after injection, the concentration of the oxidized gelonine is 300 times greater than that of the native gelonine (curve 2).

Thus, as for the A chain of ricin, these results prove that periodate oxidation has modified the sugars involved in the recognition process responsible for the elimination of the gelonine, to the point of preventing this recognition.

EXAMPLE 4

Conjugate obtained by the reaction of an antibody directed against human T cells (an antibody directed against the antigen T65), substituted by activated disulfide groups, with the oxidized A chain of ricin.

a) Antibody directed against human T cells (or antibody T101):

This antibody was obtained by the method described in Journal of Immunology, 1980, 125(2), 725-737.

b) Oxidized A chain of ricin:

The A chain of ricin was prepared in the manner indicated in Example 1.

II) Activated antibodies directed against human T cells 20 microliters of a solution containing 60.3 mg/ml of 1-ethyl-3-dimethylaminopropyl-3-carbodiimide are added to 100 microliters of a solution containing 20 mg/ml of 3-(pyridin-2-yldisulfanyl)propionic acid in tert.-butanol, and the mixture is left for 3 minutes at room temperature. 68 microliters of the solution thus obtained are added to 2 ml of an antibody solution containing 8.9 mg/ml in PBS buffer. The mixture is stirred for 15 minutes at 30° C. and then dialyzed against PBS buffer at 4° C. After dialysis, the protein solution is centrifuged to give 15 mg of activated antibody at a concentration of 7.9 mg/ml. By spectrophotometric analysis at 343 nm of the pyridine-2-thione released by exchange with 2-mercaptoethanol, it is found that the antibody obtained carries 3.8 activated mixed disulfide groups per mol of antibody.

III) Preparation of the immunotoxin containing prolonged-action A chain of ricin 2.46 ml of modified A chain containing 2.87 mg/ml are added to 1.5 ml of the solution of activated antibody obtained above (concentration: 7.9 mg/ml, i.e. 11.8 mg of activated antibodies) and the mixture is incubated for 20 hours at 20° C. The solution is centrifuged and then purified by filtration on a Sephadex G100 column, the optical density of the effluent being measured at 280 nm. Combination of the fractions containing both the antibody and the A chain gives 15 ml of immunotoxin solution containing 0.7 mg/ml, i.e. 10.5 mg. This solution contains 0.14 mg of oxidized A chain coupled with the antibody per ml.

The average degree of coupling in this preparation is therefore 1.2 mol of oxidized A chain per mol of antibody.

The immunotoxin containing oxidized A chain of ricin, IT (A-1a) T101, obtained as indicated above, was studied for its pharmacokinetic properties and its specific cytotoxicity properties towards the target cells.

EXAMPLE 5

This example demonstrates the acquisition of the property of slow plasma elimination of the immunotoxins containing prolonged-action A chain of ricin, which are abbreviated to IT(A-1a) T 101.

I—Procedure

The conjugate prepared by the procedure explained in Example 3 is administered to rabbits by a single injection into a vein in the ear. The quantity injected corresponds to 0.415 mg/kg, expressed as A chain. Blood samples are taken at intervals on heparin. The plasmas are analyzed with the aid of a radioimmunometric test with two sites, which is abbreviated below to RIM-3.

This assay is carried out by the same technique as that used for the test RIM-1, except that the solution Ac2 is a solution of goat antibodies directed against mouse IgG, purified by affinity chromatography and radiolabeled as described for the technique RIM-1. The concentration of modified immunotoxin in the samples to be determined is measured by reference to a calibration curve established by introducing the modified immunotoxin at different known concentrations. The assay RIM-3has the same reliability and reproducibility characteristics as described for the technique RIM-1.

By way of comparison, a control study is carried out under the same conditions with the conjugate called IT T101, which is obtained by the reaction of the same antibody T101, substituted by activated disulfide groups, with the native A chain of ricin. The preparation and the cytotoxic properties of this conjugate have been described in French Patent Application No. 81/21836.

The results of these experiments are represented in the same way as for the uncoupled A chain of ricin in Example 1.

II—Results

Figure 4:
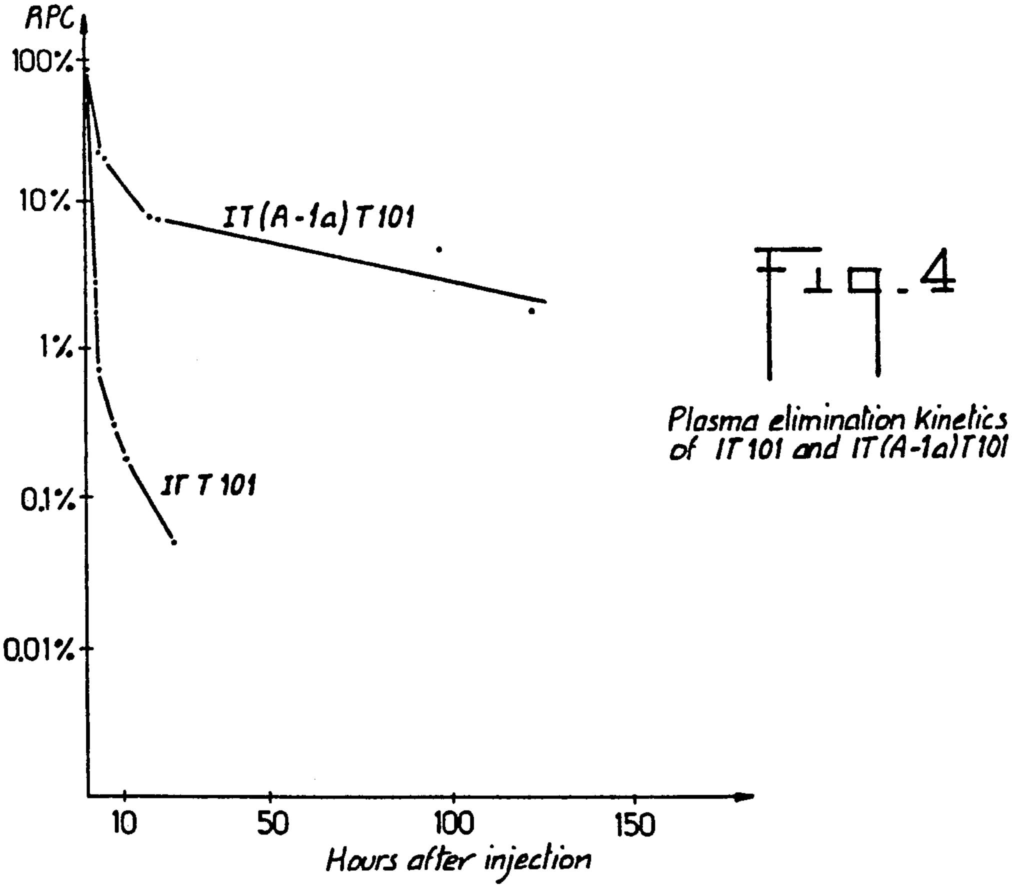
FIG. 4 shows the plasma elimination curves of IT101 and IT(A-1a)T101.

FIG. 4 shows the plasma elimination curves, as a function of time, for IT T101 and IT (A-1a) T101, injected intravenously. 24 hours after injection, the concentration of active immunotoxin is 140 times greater for IT (A-1a) T101 than for IR T101. This fact demonstrates that the new pharmacokinetic properties of the oxidized A chain are retained after coupling with an antibody.

EXAMPLE 6

This example demonstrates the retention of the specific cytotoxicity properties of IT (A-1a) T101 towards the target cells.

The fundamental biological property of the A chain of ricin is to inhibit protein synthesis in cells by degradation of the ribosomal sub-unit 60S. The technique uses a cell model in which the effect of the substances studied on the incorporation of $^{14}$C-leucine into cancerous cells in culture is measured.

The cells used belong to the CEM cell line derived from a human T leukemia which carries the antigen T65. The cells are incubated in the presence of the substance to be studied, and then, when incubation has ended, the degree of incorporation of $^{14}$C-leucine by the cells treated in this way is measured.

This measurement is made by a technique adapted from the one described in Journal of Biological Chemistry 1974, 249(11), 3357-3562, using the tracer $^{14}$C-leucine to determine the degree of protein synthesis. The radioactivity incorporated is determined here on the whole cells isolated by filtration.

On the basis of these determinations, it is possible to draw the dose/effect curves, plotting, on the abscissa, the molar concentration of A chain in the substances studied, and, on the ordinate, the incorporation of $^{14}$C-leucine expressed as a percentage of the incorporation by control cells in the absence of any substance affecting protein synthesis.

It is thus possible to determine, for each substance studied, the concentration which causes a 50% inhibition of the incorporation of $^{14}$C-leucine, or "50% inhibitory concentration" ($IC_{50}$).

Figure 5:
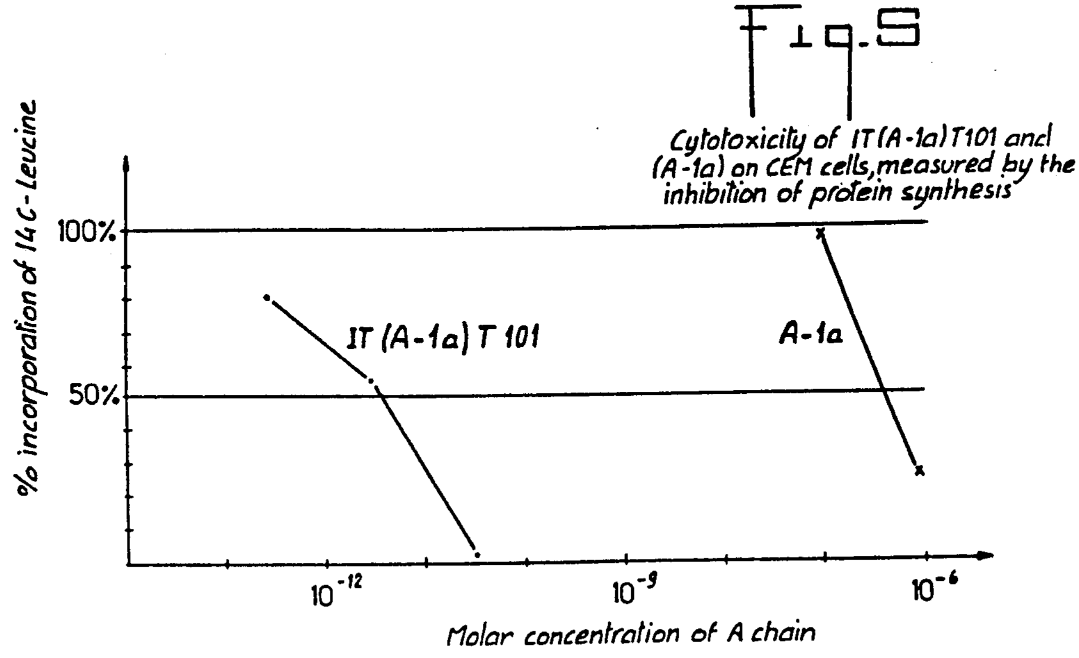
FIG. 5 shows the cytotoxicity of IT(A-1a)T101 and (A-1a) on CEM cells, measured by the inhibition of protein synthesis.

FIG. 5 shows the curves obtained in the same experiment with IT (A-1a) T101 and the uncoupled oxidized A chain in the presence of 10 mM ammonium chloride in the incubation medium. It can be seen on this figure that the IT (A-1a) T101 has a very strong cytotoxic activity ($IC_{50}=5.5\times10^{-12}$M) which is about 80,000 times greater than that of the uncoupled oxidized A chain, measured under the same conditions.

EXAMPLE 7

This example demonstrates the comparative cytotoxic efficacy of IT (A-1a) T101 and It T101 towards CEM target cells, measured in a clonogenic test.

Immunotoxins are called upon to eradicate every single one of the target cells. This performance can only be evaluated with a highly sensitive technique; tests for the inhibition of colony formation offer this possibility because a single surviving cell can be shown up among several million dead cells. This is made possible by optimum culture conditions in a gelled medium, applied to the CEM human lymphoid line.

I—Technique for measuring cytotoxicity by the inhibition of colony formation The medium used for cloning is the medium RPMI 1640 to which 1 mmol/l of sodium alpha-ketoglutarate, 1 mmol/l of sodium oxaloacetate, 5% of inactivated fetal calf serum and 10% of inactivated horse serum are added. A first, 0.3% agar solution (agarose type VII, SIGMA laboratories) is prepared in this medium, placed as a thin layer in small Petri dishes and solidified at +4° C. The cells are mixed with a second, 0.275% agar solution kept at 37° C., which is then deposited on the first layer and solidified. These concentrations of agar were chosen after a preliminary study aimed at simultaneously optimizing the cloning efficiency, the size of the colonies and the consistency of the medium. After 15 days in the incubator, the colonies are counted using an automatic colony counter ("ARTEK", DYNATECH, U.S.A.). To determine the cloning efficiency and thus the exact number of cells surviving the immunotoxin treatment, it is essential to establish a calibration line showing the number or cells inoculated as a function of the number of colonies formed. We have proved that the cloning efficiency indicated by this calibration line is practically unaffected by the presence of a high proportion of dead cells, which is the situation naturally encountered when the cells are treated with the immunotoxin.

The immunotoxin treatment is carried out by incubating the cells in the exponential growth phase and at a concentration of $10^6$/ml with the immunotoxin IT (A-1a) or IT T101 at different concentrations, in a total volume of 1ml of the medium RPMI-1640 containing 10% of inactivated fetal calf serum and 10 mmol/1of ammonium chloride. The incubation takes place at 37° C. under an atmosphere containing 5% of carbon dioxide and with horizontal shaking of the test-tubes (2500 rpm with a "GIRATORY G-2" shaker, NEW-BRUNSWICK). The cells are the washed and different dilutions are prepared, before mixing with the agar solution, so that the number of cells surviving can be measured in the zone of maximum sensitivity given by the calibration line. The results are expressed as the absolute number or cells surviving, extrapolated from the cloning efficiency, using the following relationship:

$$\text{absolute number of cells surviving: } \frac{C \times d}{E}$$

where C is the number of clones per Petri dish, d is the dilution factor of the cell preparation examined and E is the cloning efficiency established from the slope of the calibration line. Each point corresponds to the average of three tests.

II—Results

Figure 6:
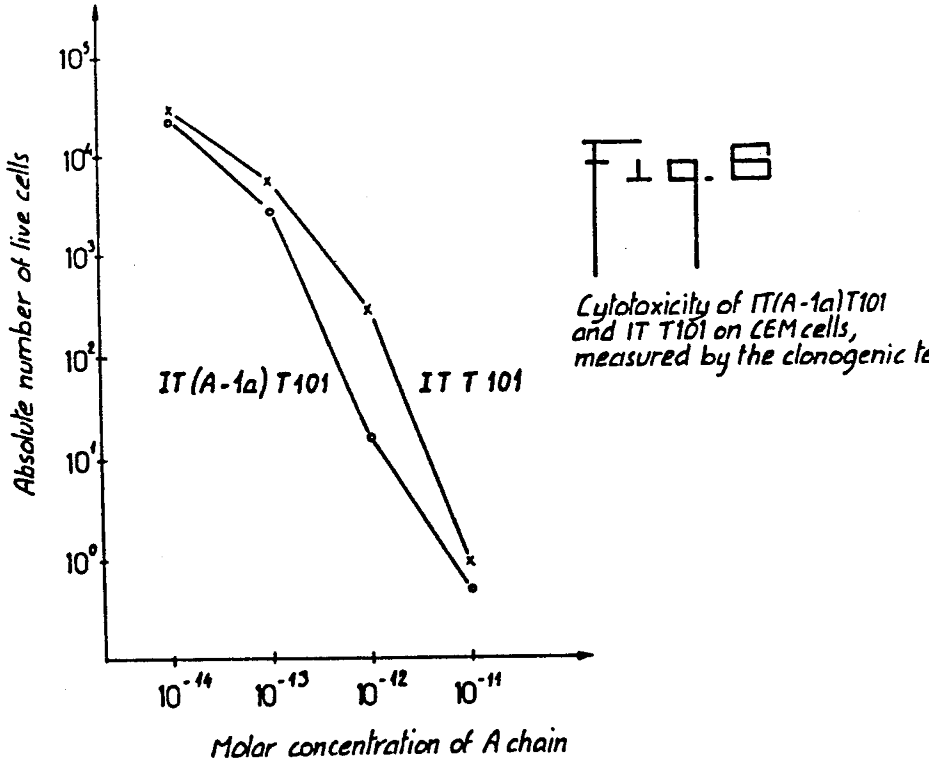
FIG. 6 shows the cytotoxicity of IT(A-1a)T101 and IT T101 on CEM cells, measured by the clonogenic test.

FIG. 6 shows the curves of the cytotoxic activity of the immunotoxins IT (A-1a) T101 and IT T101 on the CEM cells, in the presence of 10 mM ammonium chloride, as a function of the immunotoxin concentration (expressed as the molarity of A chain). It is found that the efficacies of the these two products are of the same order of magnitude. The resulting cyto-reduction is extremely large in both cases since, for concentrations as low as $10^{-11}$ M, the proportion of residual cells surviving is of the order of 0.001% of the initial value. This effect is highly specific since, at these concentrations, it was proved that the uncoupled A chain or a non-specific immunotoxin has no effect on these cells.

This example demonstrates that IT (A-1a) T101 has specific cytotoxicity properties which are virtually identical to those of conventional IT T101.

EXAMPLE 8

Toxicity of the prolonged-action A chain injected into mice

It was important to check the overall toxicological impact of the oxidized A chain on the whole animal (the toxicity of the immunotoxins being of the same order of magnitude as that of the A chain at equal molar doses). This was done by determining the 50% lethal dose of the oxidized A chain, administered intravenously to Charles River France CD1 mice, by comparison with that of the native A chain.

The values found are indicated in Table I.

TABLE I

| | $LD_{50}$ (micrograms/mouse) |
|---|---|
| Native A chain | 550 |
| Oxidized A chain | 800 |

These results show that the toxicity of the oxidized A chain is lower than that of the native A chain. This means that, despite a considerable increase in the plasma level of the A chain when the latter has been modified by oxidation, the toxicity of the product is not only not increased but, on the contrary, substantially reduced.

Immunotoxins containing modified cytotoxic subunits can therefore be used as drugs in human therapy.

These modified immunotoxins can be used for the treatment of cancerous or non-cancerous diseases where the target cells would be recognized by the antibody used to prepare the immunotoxin. The optimum administration conditions and the treatment time will have to be determined in each case according to the subject and the nature of the disease to be treated.

The new drugs according to the invention are brought into a form suitable for administration by injection and preferably intravenous injection.

What is claimed is:

1. An immunotoxin having prolonged in vivo activity comprising a conjugate in which an antibody or antibody fragment is coupled by a divalent covalent structure containing a disulfide or thioether group to a glycoprotein which inactivates ribosomes but which is not capable of binding to cells which are the target of the immunotoxin, the glycoprotein also containing carbohydrate units which have been oxidized so that the immunotoxin has prolonged in vivo activity.

2. The immunotoxin of claim 1 wherein the oxidation of the carbohydrate units of the glycoprotein is effected by periodate ions.

3. The immunotoxin of claim 2 wherein the oxidation is effected with an aqueous solution of an alkali metal periodate, for a period of 0.2 to 24 hours, at a temperature of 0 to 15 degrees C., and in the absence of light.

4. An immunotoxin having prolonged in vivo activity and having a statistical formula as follows:

P'W—GPIR—1a' in which P' represents a radical or a protein P which is an antibody or an antibody fragment; GPIR-1a' is a radical of a protein GPIR-1a which is a glycoprotein which inactivates ribosomes but which is not capable of binding to target cells, the glycoprotein also containing carbohydrate units which have been oxidized so that the immunotoxin has prolonged in vivo activity, and W represents a divalent covalent structure containing a thioether group or a disulfide group in which at least one sulfur atom of said group is from a cysteine of P, GPIR-1a or P and GPIR-1a, or at least one sulfur atom of the thioether or disulfide groups is bonded to functional groups belonging to P, GPIR-1a or P and GPIR-1a, by functional groups carried by a spacing structure of the divalent covalent structure.

5. The immunotoxin of claim 4 wherein the carbohydrate groups have been oxidized with an aqueous solution of an alkali metal periodate, for a period of 0.2 to 24 hours, at a temperature of 0 to 15 C. and in the absence of light.

6. The immunotoxin of claim 4 wherein W is W' and W' represents a divalent structure which is:

(a) a group of the formula:

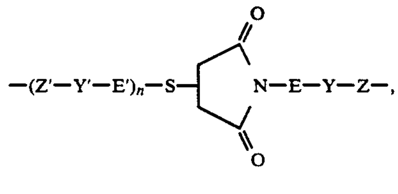

(b) a group of the formula:

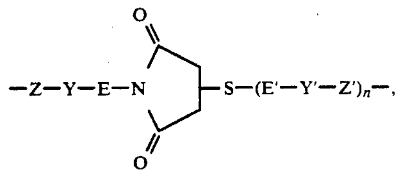

(c) a group of the formula:

$-Z-Y-E-S-S-(E'-Y'-Z')n-$ or (d) a group of the formula:

$-(Z'-Y'-E')_n-S-S-E-Y-Z-$, in which :

Z and Z' represent the functional groups belonging to the proteins GPIR-1a and P, chosen from the oxygen atom originating from the hydroxyl of one of the tyrosine residues, the carbonyl group originating from one of the terminal carboxyls or one of the free carboxyls of the aspartic and/or glutamic acids of GPIR-1a and P, the —NH— group originating from one of the terminal amines of GPIR-1a and P or from one of the amines in the epsilon position of one of the lysine residues, and, only for Z in the divalent structures (b) and (c), the group originating from the dialdehyde structure obtained after oxidation of one of the carbohydrate structures of P with periodic acid;

Y and Y' represent functional groups capable of bonding covalently with any one of the groups Z and Z' of the proteins GPIR-1a and P;

E and E' represent inert spacing structures; and n represents zero or 1.

7. An immunotoxin of claim 6 having the following statistical formula:

$P'(W'-A\text{-}1a')_m$ in which m varies from 0.3 to 12, A-1a' represents the radical of a glycoprotein which inactivates ribosomes, obtained by treatment of the A chain of ricin, in which at least one of the thiol groups of its cysteines 171 and 257 is protected, with an aqueous solution of an alkali metal periodate, for a period of 0.2 to 24 hours, at a temperature of 0 to 15 degrees C. and in the absence of light, and by deprotection of the thiol group or thiol groups and W' is as defined in claim 6.

8. An immunotoxin as claimed in claim 7, of the statistical formula:

$P'(W'-A\text{-}1a')_m$ in which W' and A-1a' are defined in claim 7, P' is an antibody fragment Fab or Fab' and m varies from 0.3 to 2.

9. An immunotoxin as claimed in claim 7, of the statistical formula $P'(W'-A\text{-}1a')_m$ in which W' and A-1a' are as defined in claim 7, P' is an antibody fragment $F(ab')_2$ and m varies from 0.5 to 4.

10. An immunotoxin as claimed in claim 7, of the statistical formula:

$P'(W'-A\text{-}1a')_m$ in which W' and A-1a' are as defined in claim 7, P' is an antibody of the IgG type and m varies from 0.5 to 6.

11. An immunotoxin as claimed in claim 7, of the statistical formula:

$P'(W'-A\text{-}1a')_m$ in which W' and A-1a' are as defined in claim 7, P' is an antibody of the IgM type and m varies from 1 to 12.

12. A prolonged-action immunotoxin according to claim 2, wherein the thiol groups of the glycoprotein are protected with protecting groups before treatment of the glycoprotein with periodate and the protecting groups are removed after periodate treatment.

13. A prolonged-action immunotoxin according to claim 4, wherein the thiol groups of the glycoprotein are protected with protecting groups as are any functional groups in the antibody portion of the immunotoxin before treatment of the glycoprotein with periodate and the protecting groups are removed after periodate treatment.

14. A prolonged-action immunotoxin according to claim 7, wherein the thiol groups of the glycoprotein are protected with protecting groups before treatment of the glycoprotein with periodate and the protecting groups are removed after periodate treatment.

15. A method of decreasing the reduction in concentration of immunotoxin per unit time in blood plasma in vivo which comprises adding an immunotoxin of claim 1 to blood plasma in vivo.

16. A process for the preparation of the immunotoxin of claim 1, wherein the disulfide or thioether bond is formed, directly or via a spacing structure, by reacting under coupling conditions an antibody or antibody fragment with a glycoprotein which inactivates ribosomes but which is not capable of binding to target cells, the glycoprotein containing carbohydrate units which have been previously oxidized so that the resulting immunotoxin of the coupling reaction has prolonged in vivo activity.

17. The process of claim 16, wherein the oxidation of the carbohydrate units is effected with an aqueous solution of an alkali metal periodate, for a period of 0.2 to 24 hours, at a temperature of 0 to 15 C. and in the absence of light.

18. A process for the preparation of an immunotoxin as claimed in claim 5, wherein a protein $P_1$, which is the prolonged-action glycoprotein which inactivates ribosomes, GPIR-1a, or an antibody or antibody fragment P, carrying at least one free thiol group attached to the said protein $P_1$ directly or via a spacing structure, is reacted, in aqueous solution and at room temperature, with a protein $P_2$, which is different from $P_1$ and is the prolonged-action glycoprotein which inactivates ribosomes, GPIR-1a, or an antibody or antibody fragment, carrying a group capable of coupling with the free thiol of the protein $P_1$, so as to form a thioether or disulfide bond.

19. A process for the preparation of an immunotoxin as claimed in claim 6, wherein a protein of the formula:

$$P_1'-(Z-Y-E-)_nSH \quad IV$$

is reacted, in aqueous solution and at room temperature, with a protein of the formula:

$P_{2'}—Z'—Y'—E'—G$ V in which $P_{1'}$ and $P_2'$ represent the radicals of the proteins $P_1$ and $P_2$ bonded to the groups belonging to said proteins, or, only if $P_1$ or $P_2$ is an antibody or antibody fragment, the radicals of the proteins $P_1$ and $P_2$ originating from the opening of the carbohydrate nuclei by reaction with periodic acid, Z, Z', Y, Y', E and E' are defined in claim 10 and G represents a group:

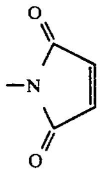

or a group —S—S—X in which X is an activating group.

* * * * *